United States Patent [19]

Pruett

[11] Patent Number: 4,918,226

[45] Date of Patent: Apr. 17, 1990

[54] PROCESS FOR CONVERTING FORMATE ESTERS TO CARBOXYLIC ACIDS

[75] Inventor: Roy L. Pruett, New Providence, N.J.

[73] Assignee: Exxon Research and Engineering Company, Florham Park, N.J.

[21] Appl. No.: 275,806

[22] Filed: Jun. 22, 1981

Related U.S. Application Data

[63] Continuation-in-part of Ser. No. 174,824, Aug. 4, 1980, abandoned.

[51] Int. Cl.⁴ .................. C07C 51/353; C07C 53/08; C07C 55/14; C07C 57/32

[52] U.S. Cl. .................. 562/607; 260/405.6; 560/234; 562/400; 562/482; 562/493; 562/496; 562/504; 562/505; 562/506; 562/509; 562/591; 562/606

[58] Field of Search .............. 562/607, 606, 504–506, 562/509, 493, 480, 405, 400, 482, 590, 591, 496

[56] References Cited

U.S. PATENT DOCUMENTS

| | | | |
|---|---|---|---|
| Re. 29,981 | 5/1979 | Isogai | 562/606 |
| 2,508,513 | 5/1950 | Groombridge | 562/607 |
| 2,739,169 | 3/1956 | Hagemeyer | 562/606 |
| 3,488,383 | 1/1970 | Coffey | 560/248 |
| 3,798,267 | 5/1974 | Wakamatsa et al. | 562/607 |
| 3,839,428 | 10/1974 | Isogai | 562/607 |
| 4,194,056 | 3/1980 | Antoniades | 562/517 |

FOREIGN PATENT DOCUMENTS

| | | | |
|---|---|---|---|
| 2109025 | 9/1971 | Fed. Rep. of Germany | 562/607 |
| 1286224 | 8/1972 | United Kingdom | |

OTHER PUBLICATIONS

Mizorogi, Shokubai (Catalysts), 19, pp. 90–05, (1977).
F. J. Bryant et al, Preprints Div. Petr. Chem., 18i, 193, (1973).
Chem. Abstr. 85, 93872d, (1976).
Chem. Abstr. 79, 78102k, (1973).

*Primary Examiner*—Vivian Garner
*Attorney, Agent, or Firm*—James H. Takemoto; Henry E. Naylor

[57] ABSTRACT

A process for converting formic acid esters or transesterification products thereof to carboxylic acids comprising contacting a formic acid ester of the formula $(HCOO)_n$—R where R is aliphatic, cycloaliphatic or aralkyl and n is 1 or 2 with a catalytically effective amount of a soluble iridium salt and an iodide promoter at a temperature of from about 100° C. to about 300° C. in the presence of an organic solvent containing at least one carboxylic acid.

19 Claims, No Drawings

4,918,226

PROCESS FOR CONVERTING FORMATE ESTERS TO CARBOXYLIC ACIDS

CROSS-REFERENCE TO RELATED APPLICATIONS

This is a Continuation-in-Part of U.S. patent application Ser. No. 174,824, now abandoned.

BACKGROUND OF THE INVENTION

This invention relates to a homogeneous process for the conversion of a formic acid ester or a transesterification product thereof to a carboxylic acid. More particularly, the formic acid ester or transesterification product is contacted with an iridium salt and an iodide promoter in the presence of an organic solvent containing carboxylic acid.

The direct conversion of formic aicd esters to carboxylic acids is known. U.S. Pat. No. 3,839,428 which was reissued as Re. 29,981 teaches a process for converting formic acid esters to the corresponding carboxylic acids which comprises contacting the ester with carbon monoxide (CO) at an elevated CO pressure. While the reaction will occur in the absence of a catalyst, Group VIII metals such as iron, cobalt and nickel, Group IIb metals and halogens may be advantageously employed to increase the conversion rate. U.S. Pat. No. 4,194,056 relates to a process for the preparation of acetic acid which comprises heating methyl formate in the presence of a soluble rhodium salt catalyst, halogen promoter and sufficient amounts of carbon monoxide to convert the rhodium salt into at least a monocarbonyl compound. Other metal salts such as cobalt iodide, nickel iodide and rhenium pentacarbonyl were listed as non-catalysts. Carbon monoxide is stated to be essential. British Patent No. 1,286,224 and German Offen. 2,109,025 disclose a process for producing acetic acid comprising heating methyl formate in the presence of carbon monoxide and a catalyst system containing rhodium and a halogen promoter.

U.S. Pat. No. 3,798,267 is directed to the isomerization of methyl formate to acetic acid in the presence of carbon monoxide and catalyst system consisting essentially of activated carbon and halogen promoter. F. J. Bryant et al., preprints Div. of Petr. Chem., 18i 193 (1973) describe the reaction mechanism for the conversion of methyl formate to acetic acid using carbon monoxide, a soluble rhodium complex and methyl iodide at 200° C. The reaction occurs whether or not acetic acid is initially present. U.S. Pat. No. 2,508,513 relates to the conversion of methyl formate to acetic acid. The catalysts are carbonyl forming metals or compounds plus halogens. Such catalysts are iron metals, tungsten, vanadium, antimony and bismuth. U.S. Pat. No. 2,739,169 discloses the reaction of CO and H$_2$O with olefins, alcohols, ester and ethers to produce acids. Catalysts are stated to be metal carbonyls with typical carbonyl-forming metals being Ni, Co, Fe, Cr, Mo, Ru, Pd, Pt, Re, Os and Ir.

Japan Kokai 76/65,703 (Chem. Abstr. 85,93872d) discloses that a mixture of acetic acid and methyl acetate is produced when methyl formate is heated with rhenium catalysts, halides and carbon monoxide. Japan Kokai 73/19,286 (Chem. Abstr. 79,78102k) relates to a hydroformylation reaction wherein methyl formate is heated with a CO/H mixture in N-methylpyrrolidone using CoI$_2$, FeI$_3$, RuI$_3$, RhCl$_3$ and bis(butylpyridinium) tetrabromocobaltate as catalysts to produce aldehydes.

U.S. Pat. No. 3,488,383 concerns the selective decomposition of formic acid in admixture with another aliphatic acid or ester of an aliphatic acid, e.g., methyl formate. The process comprises contacting the formic acid containing mixture with a soluble complex compound of a Group VIII metal or rhenium. The complex compound is a compound of Pt, Os, Rh, or preferably Ru or Ir. Formate esters are unreactive and may be present as part of the solvent system. Example 1 indicates that at least part of the formic acid is decomposed to H$_2$ and CO$_2$.

SUMMARY OF THE INVENTION

It has been discovered that formic acid esters can be directly converted to their corresponding carboxylic acids without the presence of carbon monoxide. The present process for preparation of carboxylic acids having the formula R(COOH)$_n$ comprises contacting a formic acid ester of the formula (HCOO)$_n$R where R is aliphatic, cycloaliphatic or aralkyl and n is 1 or 2 with a catalytically effective amount of a soluble iridium salt and an iodide promoter at a temperature of from about 100° C. to about 300° C. in the presence of an organic solvent containing at least one carboxylic acid.

In another embodiment, the present carboxylic acids having the formula RCOOH may be prepared by a process which comprises contacting formic acid and an ester of the formula R$_a$COOR where R$_a$ is aliphatic, cyclo-aliphatic, aralkyl or aryl, and R is aliphatic, cyclo-aliphatic or aralkyl with a catalytically effective amount of a soluble iridium salt and an iodide promoter at a temperature of from about 100° C. to about 300° C. in the presence of an organic solvent.

As noted above, the process of the invention does not require the presence of carbon monoxide, and the reaction can be carried out at autogenous pressure. Therefore, no special high pressure equipment is needed. Moreover, conversions of 90% or more are attainable in short reaction times.

DETAILED DESCRIPTION OF THE INVENTION

Formate esters may be converted to their corresponding carboxylic acids according to the reaction (HCOO)$_n$R→R(COOH)$_n$ where n is 1 or 2. The radical R is C$_1$–C$_{20}$ aliphatic, C$_3$–C$_{10}$ cycloaliphatic or C$_7$–C$_{15}$ aralkyl, preferably C$_1$–C$_8$ aliphatic, C$_4$–C$_8$ cycloaliphatic or C$_7$–C$_{12}$ aralkyl, more preferably C$_1$–C$_6$ alkyl, C$_2$–C$_6$ alkenyl, C$_2$–C$_6$ alkynl, C$_5$–C$_6$ cycloalkyl or C$_7$–C$_{10}$ aralkyl, and especially C$_1$–C$_6$ alkyl. Monoformate esters are preferred and methyl formate is especially preferred as the formate ester leading to acetic acid as product. Examples of other carboxylic acids which may be prepared are propionic, butyric, caproic, capric, lauric, cyclo-hexanecarboxylic and phenylacetic. Formate esters also include esters of dicarboxylic acids. An example of the formation of a dicarboxylic acid is the transformation of butanediol diformate to adipic acid according to the equation HCOO(CH$_2$)$_4$OOCH→HOOC(CH$_2$)$_4$COOH. Other examples include the conversion of hydroquinone diformate to terephthalic acid.

Suitable catalysts for the conversion of formate ester to carboxylic acid are iridium salts which are soluble in the reaction medium chosen. Iridium salts ae simple salts and compounds such as halides or oxides, and complexes containing halides, phosphines, amines including heterocyclic amines, arsines, cyanides, sulfides, esters, beta-diketonates, carboxylates, hydrido, sulfites, nitro and the like as ligands. The complexes may also be organometalic iridium complexes containing both $\sigma$ and $\pi$ bonded organic ligands, e.g., carbonyl, alkyl, alkenes and alkynes. Examples of iridium salts and complexes are $[Ir(cyclooctadiene)Cl]_2$, $Na_2IrCl_6 \cdot XH_2O$, $HIrCO[P(C_6H_5)_3]_3$, $ClIrCO(PEt_3)_2$, $IrCl_3 \cdot XH_2O$, $IrI_3 \cdot XH_2O$, $Na_3Ir(NO_2)_6 \cdot XH_2O$, $K_3Ir(CN)_6$, $[(C_5H_5)_2Ir]NO_3$, $Ir_4(CO)_{12}$, $IrH_3[P(C_6H_5)_3]_3$, 1,2,3-$py_3IrCl_3$, trans-$[Irpy_4Cl_2]Cl$ and $(C_8H_{12})_2IrSnCl_3$. Preferred salts are $[Ir(cyclooctadiene)Cl]_2$, $IrCl_3 \cdot XH_2O$, $IrBr_3 \cdot XH_2O$ and $IrI_3 \cdot XH_2O$. $[Ir(cyclooctadiene)Cl]_2$, $IrCl_3 \cdot XH_2O$ and $IrI_3 \cdot XH_2O$ are especially preferred. The symbol X indicates differing degrees of hydration and varies from 0 to 12.

Iodides generally are promoters or co-catalysts for the conversion of formic acid esters to carboxylic acids. Examples of suitable promoters include iodine, HI, alkali metal iodide, alkaline earth metal iodide, organic iodides, and $N(R^1)_4I$ and $P(R^1)_4I$ where each $R^1$ is independently hydrogen or $C_1$-$C_6$ alkyl. Preferred iodides are alkyl iodides of the formula $R^2I$, $R^2$ is $C_1$-$C_{10}$ alkyl. It is especially preferred to match the $R^2$ group with the R group in starting formate ester, e.g., methyl iodide with methyl formate, ethyl iodide with ethyl formate and so forth.

Catalyst concentrations may range from about 0.001 to 15 wt.% of iridium calculated as metal, based on the reaction mixture, preferably from 0.01 to 10 wt.%, especially 0.1 to 2 wt.%. The amount of iodide promoter is not critical, and high iodide:Ir ratios have no significant effect. Amounts in excess of about 0.5 wt.%, based on the reaction mixture may be employed, preferably from about 1 to 15 wt.%.

Suitable solvents are organic solvents. The solvent system must, however, contain at least one carboxylic acid as component thereof. Thus the solvent system may be either a carboxylic acid or a mixture of carboxylic acid with other inert organic solvents. Mixtures of carboxylic acids are also within the scope of the present invention. If the reactants are $R_aCOOR$ and formic acid, then formic acid functions as the organic solvent system while at the same time meeting the requirements for the presence of at least one carboxylic acid. No other carboxylic acids need be present in the solvent system in this instance although they may be added, if desired. Other inert organic solvents which are usable in mixtures with carboxylic acids are ethers, ketones, amides, esters, sulfoxides, and hydrocarbons. In order to simplify product processing, it is preferred to use as the carboxylic acid solvent, the carboxylic acid which results from formate ester conversion, e.g., an acetic acid solvent for the conversion of methyl formate to acetic acid. Solvent mixtures are ~1:1 or greater in the carboxylic acid:other organic solvent ratio. Ratios lower than about 1:1 are possible but may show decreased reactivity. A small amount of water such as less than about 10 wt.% may be present. Larger amounts of water lead to decreased yields of the desired product. It is preferred to have less than about 5 wt.% of water present in the reaction mixture.

While not wishing to be bound to any particular theory or reaction mechanism, the requirement for the presence of a carboxylic acid may be explained in terms of the following sequence of reactions:

$$HCOOR + R_aCOOH \rightleftharpoons R_aCOOR + HCOOH$$

$$HCOOH + catalyst \rightleftharpoons [catalyst\ complex]$$

$$[catalyst\ complex] + R_aCOOR \rightleftharpoons RCOOH + R_aCOOH + catalyst$$

where $R_a$ is the organic radical of the solvent carboxylic acid $R_aCOOH$. Suitable $R_aCOOH$ and $R_aCOOR$ are those wherein $R_a$ is $C_1$-$C_{20}$ aliphatic, $C_3$-$C_{10}$ cycloaliphatic, $C_7$-$C_{15}$ aralkyl or $C_6$-$C_{10}$ aryl, preferably $C_1$-$C_8$ aliphatic, $C_4$-$C_8$ cycloaliphatic, $C_7$-$C_{12}$ aralkyl or $C_6$-$C_{10}$ aryl, most preferably $C_1$-$C_8$ alkyl, and R is defined above. As described by the above sequence of reactions, the first step is a transesterification reaction between the formate ester and solvent carboxylic acid generating the mixed ester $R_aCOOR$ and formic acid. The latter reacts with the catalyst system to form a complex which ultimately results in product acid $RCOOH$ plus regenerating solvent acid $R_aCOOH$ and catalyst.

According to the above reaction sequence, it should be possible to start with a mixed ester of the formula $R_aCOOR$ plus formic acid to yield the desired carboxylic acid. This has been confirmed experimentally by heating formic acid and methyl propionate in the presence of methyl iodide and soluble iridium catalyst. A high yield of acetic acid was obtained.

The present process may be conducted at temperatures of from 100° to 300° C., preferably from 150° to 250° C. and especially from 170° to 220° C. Lower temperatures typically require longer reaction times and higher temperatures may result in catalyst instability.

As noted above, carbon monoxide is not necessary in the instant process. Carbon monoxide, nitrogen, Group O noble gases, carbon dioxide, hydrogen, $C_1$-$C_6$ hydrocarbons and the like may optionally be present as inert gases. Oxygen should be maintained at low levels (<50 ppm) if present.

The pressure is autogenous, i.e., that generated by the reactants and any inert gases present at the desired reaction temperature. Such pressures are typically in the range of from 0.1 to 20 MPa (1 MPa=10 atm). The pressure is not critical and greater pressures can be generated by added gas. There is generally, however, no advantage to operating at high pressures.

Reaction times may vary from 0.1 to 24 hours or more depending on the reaction parameters chosen. Reaction times of from 1 to 10 hours are suitable when operating in preferred temperature ranges.

THe process may be operated in either a batchwise or continuous mode with continuous operation being preferred. If the solvent system is the same as the carboxylic acid product, it is preferred to recycle a portion of the product to the reactor vessel.

By practicing the process of the invention, formic acid esters or the products of transesterification with solvent can be converted to their corresponding carboxylic acids at high rates of conversion without the use of carbon monoxide. Since autogenous pressures are employed, no special equipment is required and by using a carboxylic acid solvent which corresponds to the carboxylic acid product, separation and product isolation problems are minimized.

The instant process is further illustrated in the following examples.

EXAMPLE 1

A one-liter, Hastalloy-C stirred autoclave was charged with the following reactants and catalyst:
1.0 gm [Ir(COD)Cl]$_2$ (COD=1,5-cyclooctadiene)
100 gm methyl formate
250 gm propionic acid
15 ml methyl iodide The autoclave was purged with nitrogen, sealed, and heated with sitrring to 210° C., for three hours. An additional 100 gms of methyl formate was then added under nitrogen pressure. After heating for an additional three hours, the autoclave and contents were cooled and a brown liquid product was removed.

The composition of the product (449 gm total) was determined by gas phase chromatography with the use of a Perkin-Elmer ® model 910 chromatograph; the column was a 10′, ⅛″ SE-30. 158 gms of acetic acid was produced with a conversion of 90%. Propionic acid was employed as the carboxylic acid solvent in order to simplify product analysis.

EXAMPLES 2-7

The autoclave described in Example 1 was charged with 100 gm of methyl formate, 350 gm of propionic acid, 15 ml of methyl iodide and varying amounts of cyclooctadiene iridium (I) chloride. The reaction was conducted at 200° C. for two hours. At the reaction temperature, pressures of about 1.5-2.0 MPa were observed, which corresponds to the autogeneous pressure of the reactants and products. Products analysis was determined by gas chromatography (g.c.) and the results are set forth in Table I.

TABLE I

| Ex. No. | Cat-alyst | Pro-duct | HCOOCH$_3$, Unreacted | Methyl Acetate | Methyl Propionate | Acetic Acid |
|---|---|---|---|---|---|---|
| 2 | 0.13 g | 466 g | 18.8 g | ~5 g | 82 g | 24 g |
| 3 | 0.25 | 462 | 6.1 | ≦3 | 56 | 55 |
| 4 | 0.50 | 460 | nil | nil | 17 | 72 |
| 5 | 0.75 | 462 | nil | nil | 14 | 67 |
| 6 | 1.0 | 462 | nil | nil | 9 | 85 |
| 7 | 1.5 | 460 | nil | nil | 9 | 83 |

It is evident that quantities of catalyst ≧0.50 g are sufficient to cause high conversion of methyl formate to acetic acid under these specified conditions. At catalyst quantitites <0.50 g, acetic acid is still formed. However, the trans-esterification of the solvent becomes an interfering reaction.

EXAMPLES 8-11

A 300 ml, Hastalloy-C stirred autoclave was charged with 30 gm of methyl formate, 0.3 gm of [Ir(COD)Cl]$_2$, 100 gm of propionic acid solvent, and a varying amount of methyl iodide co-catalyst. The vessel and contents were heated to 210° C. for three hours, then cooled and the contents removed. Results of product g.c. analyses are given in Table II.

TABLE II

| Ex. No. | CH$_3$I | HCOOCH$_3$, Unreacted | Methyl Acetate | Methyl Propionate | Acetic Acid |
|---|---|---|---|---|---|
| 8 | 8 ml | nil | — | 1.6 | 19.9 |
| 9 | 4 | nil | — | 1.8 | 21.4 |
| 10 | 2 | 7.6 g | — | 5.1 | 14.1 |
| 11 | 1 | 2.1 | — | 1.9 | 19.6 |

These results show that in this range of high I/Ir ratios, the amount of methyl iodide has no significant effect.

Low concentrations of methyl iodide merely result in lower reaction rates with product distribution being relatively unaffected.

EXAMPLE 12

The autoclave described in Example 1 was charged with 100 gms of methyl formate, 350 gms of acetophenone, 1.0 gm of [Ir(COD)Cl]$_2$, and 15 ml of methyl iodide. After flushing with nitrogen and sealing, the contents were heated to 200° C. for two hours. The pressure at reaction temperature was constant at 1.8 MPa.

A golden solution which weighed 470 gms was isolated after cooling. The gas chromatograph of the product indicated only unreacted methyl formate and methyl iodide. This example demonstrates that carboxylic acid should be present in the solvent system.

EXAMPLE 13

A solution of 100 ml of ethyl formate, 0.40 gm of [Ir(COD)Cl]$_2$, 16 ml of methyl iodide and 250 ml of acetic acid was heated with stirring to 210° C. for four hours, then cooled and analyzed. No solid precipitate was formed during the reaction. The gas chromatographic analysis of the product showed a mixed of methyl propionate and propionic acid, with the latter predominating. The methyl propionate was formed by transesterification of unreated methyl formate with product propionic acid. This example shows that other alkyl formates are operable with the iridium catalyst system.

EXAMPLE 14

The autoclave described in Example 1 was charged with the following:
100 ml methyl formate
0.5 gm [Rh(COD)Cl]$_2$
16 ml methyl iodide
250 ml propionic acid After flushing the free space with nitrogen, the autoclave and contents were heated to 210° C. for one hour, then cooled to room temperature. The contents were discharged and found to contain large amounts of a black precipitate. Unconverted methyl formate was present but no acetic acid, although partial conversion to methyl acetate was noted.

EXAMPLE 15

Example 14 was repeated, with the experimental difference that 3 MPa of carbon monoxide was added before heating the vessel and contents. The final product was a dark red solution and no solids were detectable. The conversion to acetic acid was >50%; methyl acetate was also present, but in lesser quantities. Examples 14 and 15 confirm the prior art teaching that carbon monoxide pressure is essential for the operability of rhodium as a homogeneous catalyst.

EXAMPLE 16

The reactor described in Example 1 was charged with the following reactants and catalyst:
150 ml of methyl formate
40 ml of water
200 ml of propionic acid 10 ml of methyl iodide
0.25 gm of [Ir(COD)Cl]$_2$ The atmosphere in the reactor was flushed with carbon monoxide and pressurized to 1 MPa, then heated with stirring to 190° C. for 6 hrs. During this time, the pressure rose from 2.5 to 9.3 MPa pressure. A mass spectrograph analysis of the gas phase at the end of the reaction showed the presence of 59 mole % methane, 32 mole % carbon dioxide, 5.3 mole % hydrogen and only 0.8 mole % carbon monoxide. Approximately 1.0 mole of gaseous products were formed, which resulted from a decomposition route to CO$_2$ and methane, not CO. The liquid product solution contained unreacted methyl formate, methyl acetate and acetic acid. This example demonstrates the novel dual reaction path which results from the presence of substantial quantities of water.

EXAMPLE 17

The reactor described in Example 1 was charged with:
100 gms of methyl formate
350 gms propionic acid
15 ml methyl iodide
0.5 gm [Ir(COD)Cl]$_2$ The reactor was sealed and then pressurized with 2.0 MPa of carbon monoxide. The vessel and contents were heated to 200° C. for two hrs., during which time the pressure rose from 3.5 to 3.9 MPa. After cooling and venting the autoclave, a dark red product solution (417 gms) was removed. Analysis showed 5.7 gms of unreacted methyl formate, ~5 gms methyl acetate, 53 gms of methyl propionate and 70.5 gms of acetic acid. A comparison with Example 4 of Table I indicates that the presence of carbon monoxide has no major effect on the reaction with only perhaps a slight inhibition.

EXAMPLE 18

The autoclave described in Example 1 was charged with the following reactants and catalyst:
100 gms methyl formate
350 gms propionic acid
0.5 gm [Ir(COD)Cl]$_2$
16 ml 57% aqueous hydriodic acid The autoclave was flushed with nitrogen and heated to 200° C. for 2 hrs., during which time the pressure rose from 1.6 to 3.4 MPa. After cooling, a brown liquid (some suspended solid) was removed, wt. 450 gms. Gas chromatographic analysis showed 8.3 gms of unreacted methyl formate, 13 grams of methyl acetate and 17 grams of acetic acid. This example illustrates the use of HI as a suitable co-catalyst although the aqueous portion caused a reduction in yield.

EXAMPLE 19

The autoclave described in Example 1 was charged with a solution of the following ingredients:
100 gm methyl formate
175 gm trimethylacetic acid
0.5 gm [Ir(COD)Cl]$_2$
15 ml methyl iodide The autoclave was flushed with nitrogen and heated, with stirring, at 215° C. for four hours. After cooling, the autoclave was emptied and the contents analyzed by g.c. The product contained 65.5 gms of acetic acid and 3.2 gms of unreacted methyl formate. This example shows that other carboxylic acids, even highly hindered ones such as trimethylacetic acid, can be successfully utilized as reaction solvent.

EXAMPLE 20

The autoclave described in Example 1 was charged with a solution containing the following ingredients:
100 ml methyl formate
175 ml propionic acid
75 ml methyl propionate
0.25 gm [Ir(COD)Cl]$_2$
10 ml methyl iodide The autoclave was sealed under 1 MPa of nitrogen and the contents were heated with stirring to 200° C. for 2 hrs. The pressure remained at 3.0–3.2 MPa throughout the reaction time. After cooling, the contents were removed and analyzed by g.c. This showed approximately equal weights of unreacted methyl formate and of methyl acetate plus acetic acid.

EXAMPLE 21

Example 20 was repeated except that the quantities of propionic acid and methyl propionate were 75 ml and 175 ml, respectively. The product showed much more unreacted methyl formate, with the quantity of methyl acetate and acetic acid about 30% of the amount of unreacted methyl formate.

EXAMPLE 22

The autoclave as described in Example 1 was charged with a solution of the following:
0.5 gm [Ir(COD)Cl]$_2$
100 gm methyl formate
250 gm pentanoic acid
15 ml methyl iodide The autoclave was flushed with nitrogen, sealed, and heated to 200° C. with stirring. After two hours at this temperature, heating was discontinued and the autoclave and contents were cooled. The contents were analyzed by g.c. and found to contain 9.3 gms of unreacted methyl formate and 36.1 gms of acetic acid. This example demonstrates that longer chain carboxylic acids can be used as solvent.

EXAMPLE 23

The autoclave as described in Example 1 was charged with:
0.50 gm [IR(COD)Cl]$_2$
100 gms methyl formate
50 gms acetophenone
200 gms propionic acid
15 ml methyl iodide The autoclave was flushed with nitrogen, sealed and heated to 215° C. with stirring. After two hours at this temperature, the autoclave was cooled and the contents removed. Analysis by g.c. showed the product to contain 13.5 gms of unreacted methyl formate and 14.1 gms of acetic acid. This example shows that mixtures of carboxylic acids and other solvents, such as acetophenone are operable.

EXAMPLE 24

A one-liter, Hastalloy-C stirred autoclave was charged with the following reactants and catalyst:
0.5 gm. [IR(COD)Cl]$_2$
50 gms. 95–97% formic acid
88 gms. methylpropionate
250 gms. propionic acid 10 ml methyl iodide After purging with nitrogen, the vessel and contents were heated, with stirring, at 200° C. for five hours. They were then cooled to room temperature and contents were removed.

The dark red solution, 402 gm., was analyzed by gas-liquid chromatography and found to contain no significant quantity of methyl formate, 10.9 gm. of methyl acetate, 3.3 gm. of unreacted methyl propionate and 311 gm. of propionic acid. The yield of acetic acid was 42 gm.

EXAMPLE 25

The experimental procedure, Example 24, was repeated, except that the materials charged into the reactor were:
0.50 gm. [Ir(COD)Cl]$_2$
123 gms. methyl acetate
77 gms. formic acid
150 gms. acetic acid
7 ml methyl iodide After heating at 200° C. for four hours, the solution was cooled and analyzed as before. The yield of acetic acid was nearly quantitative; only a small amount of methyl acetate remained unconverted.

EXAMPLE 26

The one-liter autoclave of Example 24 was charged with the following materials in a glass liner:
0.24 gm. [Rh(COD)Cl]$_2$
45 gms. 95–97% formic acid
67 gms. methyl acetate
150 gms. propionic acid
2 ml methyl iodide After heating under a nitrogen atmosphere at 200° C. for three hours, the solution was cooled and removed. Black solid and a black precipitate on the walls of the liner were present. Analysis of the dark red solution showed no glc peak for acetic acid. Large amounts of unreacted methyl acetate were present. This experiment shows that rhodium is an unsatisfactory catalyst for the reaction.

EXAMPLE 27

Example 26 was repeated with the autoclave charged with the following in a glass liner:
0.30 gm. [Ir(COD)Cl]$_2$
42 gms. 95–97% formic acid
67 gms. methyl acetate
150 gms. propionic acid
6 gms. of a solution which resulted from the addition of 2 ml of methyl iodide to 140 gms. of propionic acid After sealing under a nitrogen atmosphere, the solution was heated at 190° C. with stirring, for four hours. During this time, the pressure in the autoclave rose from 1.1 to 1.9 MPa. The solution was then cooled and removed from the autoclave. There was present 256 gms. of a dark solution mixed with a black solid.

Analysis of the solution by glc, with ethyl benzoate as internal standard, showed the presence of 23 gms. of acetic acid (21% of theory), together with 26.8 gms. of unreacted methyl acetate, 9.9 gms. of methyl formate and 29.4 gms. of methyl propionate. This amount of methyl iodide promoter (0.14 I/Ir) is sufficient to catalyze the reaction, but not sufficient to maintain a stable solution.

EXAMPLE 28

Example 27 was repeated except that the reactants were varied as follows:
0.50 gm. [Ir(COD)Cl]$_2$
70 gms. 95–97% formic acid
111 gms. methyl acetate
200 gms. propionic acid
60 gms. of a solution which resulted from the addition of 2 ml of methyl iodide to 140 gms. of propionic acid.

After sealing under a nitrogen atmosphere and heating at 190° C. with stirring for four hours, the solution was cooled and removed from the autoclave. It was a dark red solution, weight 423 gms. Analysis by glc with ethyl benzoate as standard indicated the composition to be 7.9 gms. methyl formate, 29.1 gms. of unreacted methyl acetate, 45.5 gms of methyl propionate, 70.3 gms of acetic acid (39% yield) and 196 gms. of propionic acid. This experiment shows that this amount of methyl iodide promoter (14 I/Ir) is sufficient to catalyze the reaction and to maintain catalyst stability.

EXAMPLE 29

The one-liter autoclave was charged with the following reactants:
0.5 gm [Ir(COD)Cl]$_2$
102 gms. isopropyl acetate
50 gms. 95–97% formic acid
250 gms. acetic acid
10 ml methyl iodide After sealing under a nitrogen atmosphere, the autoclave and contents were heated at 200° C. for five hours. They were then cooled to ambient temperature and the contents were discharged. Analysis indicated the presence of C$_4$ acids.

EXAMPLE 30

A one-liter Hastalloy-C, stirred autoclave was charged with the following reactants, catalyst and solvent:
0.50 gm. cyclooctadiene iridium (I) chloride
15.9 gms. methyl iodide
74 gms. (1.0 mole) methyl acetate
60 gms. (1.2 mole) 95–97% formic acid
25 gms. acetophenone The vessel was purged with nitrogen, sealed and heated with stirring to 200° C. After four hours at this temperature, the vessel was cooled to ambient conditions and the contents (light yellow, 378 gms.) were removed and analyzed by glc, a thermal conductivity detector was used, with a Poropak T ® column and dimethyl formamide as internal standard. Analysis showed the presence of:
24.5 gms. HCOOCH$_3$ (0.41 mole)
34.5 gms. CH$_3$COOCH$_3$ (0.47 mole)
23.9 gms. HCOOH (0.52 mole)
50.5 gms. CH$_3$COOH (0.84 mole)

The portion of the methyl acetate which had reacted was 0.53 mole, which should produce 1.06 moles of acetic acid at 100% yield. The 50.5 gms. acetic acid actually produced was 75% of theory.

This example shows that carboxylic acids, other than the reactant formic acid, are not required as part of the solvent system if the transesterification products are used as reactants.

EXAMPLES 31-39

In examples 31-35, the catalyst and promoter were 0.5 gm. [Ir(COD)Cl]$_2$ and 22.5 gm. CH$_3$I, the solvent was 250 gm. propionic acid and the reaction was conducted at 180° C. for 4 hours. Ninety-six grams of 95-97% formic acid was used along with variable amounts of methyl propionate. Table III summarizes the results.

TABLE III

| Expt. No. | CH$_3$CH$_2$COOCH$_3$ gms. | Acetic Acid Produced gms., Yield |
|---|---|---|
| 31 | 33 | 19.7, 84% |
| 32 | 44 | 28.1, 94% |
| 33 | 55 | 37.0, 99% |
| 34 | 66 | 41.6, 92% |
| 35 | 88 | 53.2, 89% |

In Examples 36-39, the reaction conditions included 110 gms. methyl propionate, 0.50 gm. [Ir(COD)Cl]$_2$, 22.7 gms. methyl iodide, 300 gms. propionic acid, 180° C., 4 hours. Variable amounts of 95-97% formic acid were used. The results are given in Table IV.

TABLE IV

| Expt. No. | 95-97% HCOOH, gms. | Acetic Acid Produced gms., Yield |
|---|---|---|
| 36 | 12 | 6.0, 40% |
| 37 | 21 | 12.6, 48% |
| 38 | 36 | 23.7, 53% |
| 39 | 48 | 31.7, 53% |

In each of the above cases, unreacted formic acid and the ester methyl formate were present at the end of the four hour period. Correcting for these unreacted components gave selectivities to acetic acid which were nearly quantitiative. This shows that reactions employing less than theoretical amounts of formic acid are slow, but do not have lower efficiency to acetic acid.

EXAMPLE 40

A one-liter, Hastalloy C, stirred autoclave was charged with:
0.50 gm. [Ir(COD)Cl]$_2$
30 ml. n-butyl iodide
132 gm. methyl propionate
73 gm. 95-97% formic acid
300 gm. propionic acid The vessel was purged nitrogen, sealed, and heated with stirring to 170° C. and held at that temperature for 5 hours. After cooling to ambient conditions, the contents of the vessel were removed and analyzed by glc. The yield of acetic acid was 27.2 gm. (30%). However, unreacted components included 7.8 gms. methyl formate, 48.7 gms. methyl propionate and 34.1 gms. formic acids. Thus the efficiency to acetic acid, based on methoxy groups converted to acid, was 56%. This experiment shows that iodine compounds other than methyl iodide may be used.

EXAMPLES 41-45

A one-liter Hastalloy-C, stirred autoclave, was charged with the following materials:
0.50 gm of cyclooctadiene iridium (I) chloride
96 gm of 95-97% formic acid
66 gms of methyl propionate
300 gms of propionic acid methyl iodide
(Example 41) 1 gm
(Example 42) 2.3 gms
(Example 43) 4.6 gms
(Example 44) 11.4 gms
(Example 45) 22.7 gms In each example, the vessel was flushed with nitrogen, sealed, and heated at 180° C. for four hours. Samples were removed after 0.5 hours, 1 hr., 2 hr., and 4 hours. Each sample, as well as the final solution, was analyzed by glc. The amount of acetic acid formed is given in Table V.

TABLE V

| | Acetic Acid Formed, gms | | | |
|---|---|---|---|---|
| Example No. | 0.5 hr. | 1.0 hr. | 2.0 hr. | 4.0 hr. |
| 41 | 5.3 | 5.6 | 7.9 | 13.9 |
| 42 | 5.1 | 7.7 | 12.5 | 23.0 (51%) |
| 43 | 6.9 | 10.0 | 18.3 | 31.9 |
| 44 | 12.2 | 18.3 | 33.3 | 41.4 |
| 45 | 13.1 | 23.6 | 37.4 | 43.8 (97%) |

The examples in Table V show that amounts of iodide about 0.2 wt.% are operable. Acetic acid production is low, even after four hours reaction time. When the amount of iodide is about 1 wt.% or above, conversions are good and above about 2.5 wt.%, no particular advantage is gained.

What is claimed is:

1. A process for the preparation of carboxylic acids of the formula R(COOH)$_n$ which comprises contacting a formic acid ester of the formula (HCOO)$_n$-R where R is aliphatic, cycloaliphatic or aralkyl and n is 1 or 2 with a catalytically effective amount of a soluble iridium salt and an iodide promoter at a temperature of from about 150° C. to about 250° C. in the presence of at least one carboxylic acid as solvent, at a pressure autogeneously present in the contacting step, and optionally in the presence of inert gas, but in the substantial absence of carbon monoxide.

2. A process for preparing carboxylic acids of the formula R-COOH which comprises contacting formic acid and an ester of the formula R$_a$COOR where R$_a$ is aliphatic, cycloaliphatic, aralkyl or aryl, and R is aliphatic, cycloaliphatic or aralkyl with a catalytically effective amount of a soluble iridium salt and an iodide promoter at a temperature of from about 150° C. to about 250° C. in the presence of a carboxylic acid solvent, at a pressure autogeneously present in the contacting step, and optionally in the presence of inert gas, but in the substantial absence of carbon monoxide.

3. The process of claim 2 wherein R$_a$ is C$_1$-C$_{20}$ aliphatic, C$_3$-C$_{10}$ cycloaliphatic, C$_7$-C$_{15}$ aralkyl or C$_6$-C$_{10}$ aryl.

4. The process of claim 2 wherein the solvent is formic acid.

5. The process of claims 1 or 2 wherein R is C$_1$-C$_{20}$ aliphatic, C$_3$-C$_{10}$ cycloaliphatic or C$_7$-C$_{15}$ aralkyl.

6. The process of claim 5 wherein R is methyl.

7. The process of claim 1 wherein n is 1.

8. The process of claims 1 or 2 wherein the iridium salt is an iridium complex containing halide, phosphine, amine, arsine, cyanide, sulfide, ester, beta-diketonate, carboxylate, hydrido, sulfite, nitro, carbonyl, alkyl, alkenyl and alkynyl as ligands.

9. The process of claims 1 or 2 wherein the iridium salt is selected from the group consisting of [Ir(cyclooctadiene)Cl]$_2$, IrCl$_3$·xH$_2$O and IrI$_3$·xH$_2$O.

10. The process of claim 9 wherein the iridium salt is IrI$_3$·xH$_2$O.

11. The process of claims 1 or 2 wherein the iodide promoter is selected form the group consisting of iodine, HI, alkali metal iodide, alkaline earth iodide, organic iodide and $N(R^1)_4I$ and $P(R^1)_4I$ where each $R^1$ is independently H or $C_1$-$C_6$ alkyl.

12. The process of claim 11 wherein the organic iodide has the formula $R^2I$ where $R^2$ is $C_1$-$C_{10}$ alkyl.

13. The process of claims 1 or 2 wherein the catalyst concentration is from 0.001 to 15 wt. %, based on the reaction mixture.

14. The process of claims 1 or 2 wherein the carboxylic acid is a $C_1$-$C_8$ acid.

15. The process of claim 1 wherein the solvent is acetic acid.

16. The process of claims 1 or 2 wherein the carboxylic acid as solvent is the same as the carboxylic acid produced from formic acid ester conversion.

17. A process for the preparation of acetic acid which comprises contacting methyl formate with a catalytically effective amount of a soluble iridium salt selected from the group consisting of $(Ir(cyclooctadiene)Cl)_2$, $IrCl_3 \cdot XH_2O$ and $IrI_3 \cdot XH_2O$ and an iodide promoter at a temperature of from about 150° C. to about 250° C. in the presence of an acetic acid solvent, at a pressure autogeneously present in the contacting step, and optionally in the presence of inert gas, but in the substantial absence of carbon monoxide.

18. A process for the preparation of acetic acid which comprises contacting methyl acetate and formic acid with a catalytically effective amount of a soluble iridium salt selected from the group consisting of $(IR(cyclooctadiene)Cl)_2$, $IrCl_3 \cdot XH_2O$ and $IrI_3 \cdot XH_2O$ and an iodide promoter at a temperature of from about 150° C. to about 250° C. in the presence of a formic acid solvent, at a pressure autogeneously present in the contacting step, and optionally in the presence of inert gas, but in the substantial absence of carbon monoxide.

19. A process for the preparation of acetic acid which comprises contacting methyl formate with a catalytically effective amount of $IrI_3 \cdot XH_2O$ or $IrCl_3 \cdot XH_2O$ and a methyl iodide promoter at a temperature of from about 170° C. to about 220° C. in the presence of an acetic acid solvent, at a pressure autogeneously present in the contacting step, and optionally in the presence of inert gas, but in the substantial absence of carbon monoxide.

* * * * *